United States Patent [19]

Winder

[11] Patent Number: 4,812,121

[45] Date of Patent: Mar. 14, 1989

[54] MANDIBULAR DENTURE STABILIZER

[76] Inventor: George C. Winder, 33 Regency Square, Scarborough, Ontario, Canada, M3K 1G8

[21] Appl. No.: 192,172

[22] Filed: May 10, 1988

[51] Int. Cl.[4] .............................................. A61C 13/22
[52] U.S. Cl. .................................................... 433/172
[58] Field of Search ......................... 433/167, 172, 229

[56] References Cited

U.S. PATENT DOCUMENTS

| | | | |
|---|---|---|---|
| 1,153,486 | 9/1915 | Gregg | 433/177 |
| 1,327,674 | 1/1920 | Hinchey | 433/172 |
| 1,732,898 | 10/1929 | Krasnoff | 433/177 |
| 1,792,226 | 2/1931 | Krasnoff | 433/184 |
| 1,801,040 | 4/1931 | Fogg | 433/172 |
| 1,910,292 | 5/1933 | Julian | 433/172 |
| 2,043,742 | 6/1936 | Fleischman | 433/177 |
| 2,250,373 | 7/1941 | Hagerman | 433/177 |
| 3,023,499 | 3/1962 | Michaelides | 433/172 |
| 3,092,778 | 6/1963 | Mailland | 328/165 |
| 4,609,355 | 9/1986 | Harvey, Sr. et al. | 433/181 |

Primary Examiner—Robert Peshock
Attorney, Agent, or Firm—Nixon & Vanderhye

[57] ABSTRACT

A method and apparatus for stabilizing a mandibular denture. The stabilizer comprises an anchor means adapted to be secured to said lingual flange, appendage means adapted to fit under the patient's tongue and fitting means adapted to permit adjustment of the position of the appendage means relative to the anchor means.

9 Claims, 5 Drawing Sheets

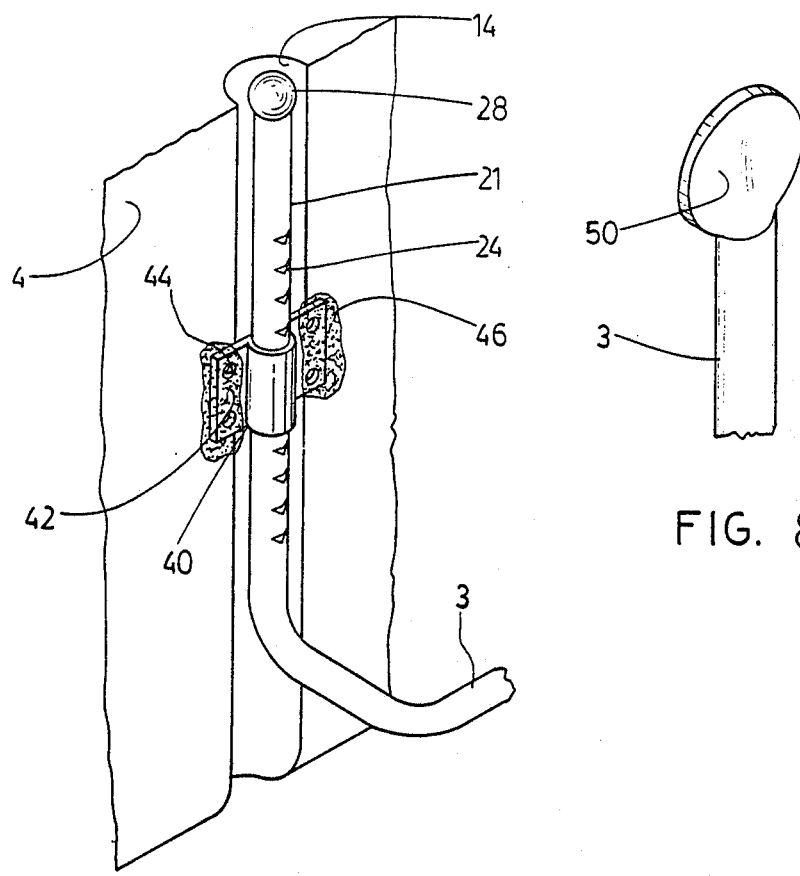
FIG. 7
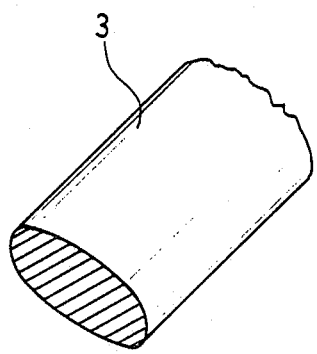
FIG. 8
FIG. 9

MANDIBULAR DENTURE STABILIZER

This invention relates to mandibular denture prosthesis and in particular to an improvement to a mandibular denture having means to allow a person to stabilize the full denture in his mouth on his lower ridge by means of tongue pressure.

Many people who wear removable mandibular prosthetic appliances (dentures) experience difficulty, discomfort and even embarrassment because of movement of their denture base in their mouth while chewing or talking. This problem is particularly acute where the person's lower alveolar ridge is severely resorbed (smooth and flat) and offers little resistance to movement of the denture base.

In the prior art a number of means have been attempted to solve this problem including the use of pastes which bond the plate to the gum and other such means. Examples of devices located in a prior art search are found in:

U.S. Pat. No. 1,153,486 which issued to Gregg on Sept. 14, 1915 entitled "Artificial Denture"

U.S. Pat. No. 1,327,674 which issued to Hinchey on Jan. 13, 1920 entitled "Denture"

U.S. Pat. No. 1,732,898 which issued to Krasnoff on Oct. 22, 1929 entitled "Artificial Denture"

U.S. Pat. No. 1,801,040 which issued to Fogg on Apr. 14, 1931 entitled "Artificial Denture"

U.S. Pat. No. 1,792,226 which issued to Krasnoff on Feb. 10, 1931 entitled "Artificial Denture"

U.S. Pat. No. 1,910,292 which issued to Julian on May 23, 1933 entitled "Dental Appliance"

U.S. Pat. No. 2,043,742 which issued to Fleischman on June 9, 1936 entitled "Self-Retaining Lower Denture"

U.S. Pat. No. 2,250,373 which issued to Hagerman on July 22, 1941 "Dental Plate"

U.S. Pat. No. 3,094,778 which issued to Mailland on June 25, 1963 entitled "Artificial Denture"

U.S. Pat. No. 4,609,355 which issued to Harvey on Sept. 2, 1986 "Dental Prosthesis and Method"

Of particular interest to this invention, however, is a disclosure by Milner in U.S. Pat. No. 1,534,802 which issued Apr. 25, 1925. Milner disclosed wire frames which project inward from the lingual flange of the denture plate to extend under the tongue of the person wearing the plate. Milner taught that the downward pressure of the tongue on the wire frame could transmit sufficient pressure to the denture to help secure it on the lower gum ridge.

Notwithstanding that Milner's patent issued more than years ago, the inventor of the present invention has found no evidence that the Miner concept ever attained any significant commercial success. It is not known to be in practice currently. The present inventor experimented with the concept but found that while it had advantages as claimed by Milner, it had a significant disadvantage in that it did not seem to be practical in the form disclosed by Milner for commercial use or manufacture. The primary disadvantage of Milner's device, as perceived by the present inventor, was that there was no allowance made for the fact that each person's mouth has a different size and shape. Milner did not disclose any means which would permit dentists or other dental personnel (e.g. denturist) to install the stabilization means disclosed by Milner into a full mandibular denture base while permitting adjustment to fit the mouth of an individual patient. Milner's wire frame had to be bonded in place before it was first worn by a patient, therefore the first fitting had to be made from measurements in the mouth and had to be exact. Moreover, each wire frame had to be custom made to fit the mouth of each patient. There did not appear to be any practical way to manufacture such devices in quantity at low cost to be fitted with little effort to the mouths of many persons.

The present invention is an improvement on Milner's concept to overcome these deficiencies to permit commercial use and manufacture. In the mandibular denture of the present invention there is provided a set of appendages which protrude bilaterally and medially (laterally inward) from the lingual flange. These appendages are adapted to fit under the tongue to stabilize and secure the mandibular denture in the mouth of the patient. The appendages have an adjustable fitting means adapted to permit positioning of the appendages in the mouth of a patient.

The word "appendage(s)" is used in this specification as a word of general scope to describe devices which extend medially from the lingual flange of the mandibular denture under the tongue of a denture wearer to receive downward pressure from the tongue and transmit that pressure to the denture base thereby providing active and passive stability to the mandibular denture. It is preferred that the appendages be made of wire because they are readily self-cleansing. However, it will be appreciated that other similar means may be used whether made of plastic or other suitable materials or whether comprising full shapes such as "plates" or flanges extending under the tongue rather than wire frames.

It will be appreciated by those skilled in the art that the appendages will preferably be made of some material relatively inert in a patient's mouth such as stainless steel, chromium cobalt, ticonium, vitalium or titanium or gold or gold plated material.

The adjustable fitting means of this invention may be constructed in a number of different ways using any of a variety of known adjustable mechanisms suitable for the purposes described herein and compatible with use in the mouth of a patient.

In one embodiment of the invention the adjustable fitting means is found at each end of the appendage where it joins the lingual flange. Each such end terminates in a threaded sleeve adapted to receive a threaded shaft (or retention rod) mounted rotatably on a pintle which in turn is mounted on an anchor. The anchor is adapted to be bonded into the lingual flange of the mandibular denture. The retention rod is adapted to protrude downwardly and inwardly (medially) from the anchor and to rotate freely on the pintle. The sleeve is adapted to fit about a retention rod in threaded connection. Each rod being rotatably mounted on the pintle, is adapted to be turned within a sleeve by a screwdriver or like means to advance the appendage in either direction of the longitudinal axis of the shaft. Thus, by the combination of this invention, the appendages may be fixed to the denture by bonding the anchors to the lingual flange then the appendages may be adjusted to fit the mouth of the patient. When a comfortable fitting is obtained, the adjustable fitting mechanism may be covered with material similar to that of the lingual flange or other suitable material to set the fitting permanently.

With the advantages of this combination a manufacturer of appendages intended for implantation in dentures need not be concerned with manufacturing individual pieces for each patient. With a few standard sizes, each having adjustment means of this invention, virtually all patients' requirements may be met.

A dentist or dental laboratory attempting to fit the appendages into a denture need not be concerned about trying to bond the anchors in an exact position on the basis of measurements previously taken in the patient's mouth. The anchors of appendages may be implanted in close proximity to the optimum position and adjustments may be made after bonding of the anchors to fit the individual patient.

The patient has an opportunity to have the appendages fitted to his mouth, to try them for a period of time and to have them readjusted, if necessary, until they are comfortable. After the best fit or position is obtained, the retention rods and sleeves may be covered and bonded into the lingual flange to permanently secure the fitting, to shield the mechanism from food and to protect the patient's mouth from irritation from the threaded rod.

In another embodiment of this invention there is provided a gear within the sleeve which interacts with gear teeth in the surface of the retention rod. The gear within the sleeve may be rotated by a screwdriver or other means.

In other embodiments of this invention the adjustment feature is achieved by friction fit devices of various constructions. The friction fit construction typically has a simpler design than the threaded shaft and sleeve embodiment and therefore the cost of manufacture is reduced. In these embodiments there is typically a collar or sleeve means which is anchored into the lingual flange by bonding it into a slot ground in the lingual flange. The ends of the wire frame or appendage, which may be called retention rods, are then mounted slidably within the sleeve means to be adjusted to the correct fit. Temporary fixation of the appendage during the adjustment procedure may be achieved by friction between the moveable parts or by fasteners affixed to the sleeve means which clamp the retention rods or catch onto notches or ridges in same. Glues or other suitable bonding material may be used to effect temporary fixation as well. In the friction fit constructions, stop means is also provided to prevent the retention rods from completely disengaging from the sleeve means to prevent the appendage from accidentally dislodging into the patient's mouth during the fitting procedure.

In the figures which illustrate the preferred embodiment of this invention,

FIG. 7 shows the open sided sleeve in combination with the appendage of this invention;

FIG. 8 shows a wire stop of flattened wire;

FIG. 9 illustrates a cross section of an elliptical wire for use in this invention.

In the figures, like numbers indicate like elements.

Figure 1:
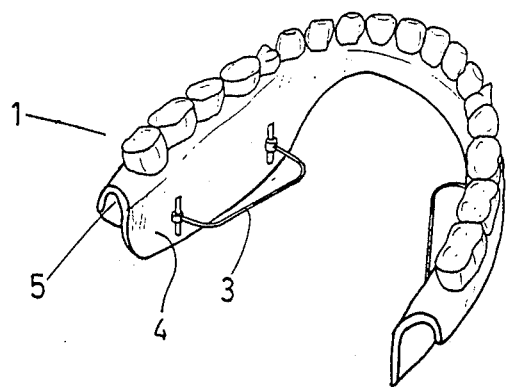
FIG. 1 depicts the mandibular denture having the adjustable stabilization means of this invention.

As illustrated in FIG. 1, the mandibular denture (1) is fitted with stabilization means comprising appendages (3) attached to the inner wall of the lingual flange (4). The mandibular denture (1) rests on the lower ridge or alveolar ridge of a patient along the denture fitting surface (5). The purpose of the stabilizing appendages (3) is to receive tongue pressure to press the mandibular denture (1) onto the gum to more securely seat the fitting surface (5) about the alveolar ridge and thereby stabilize the denture in the mouth.

Figure 2:
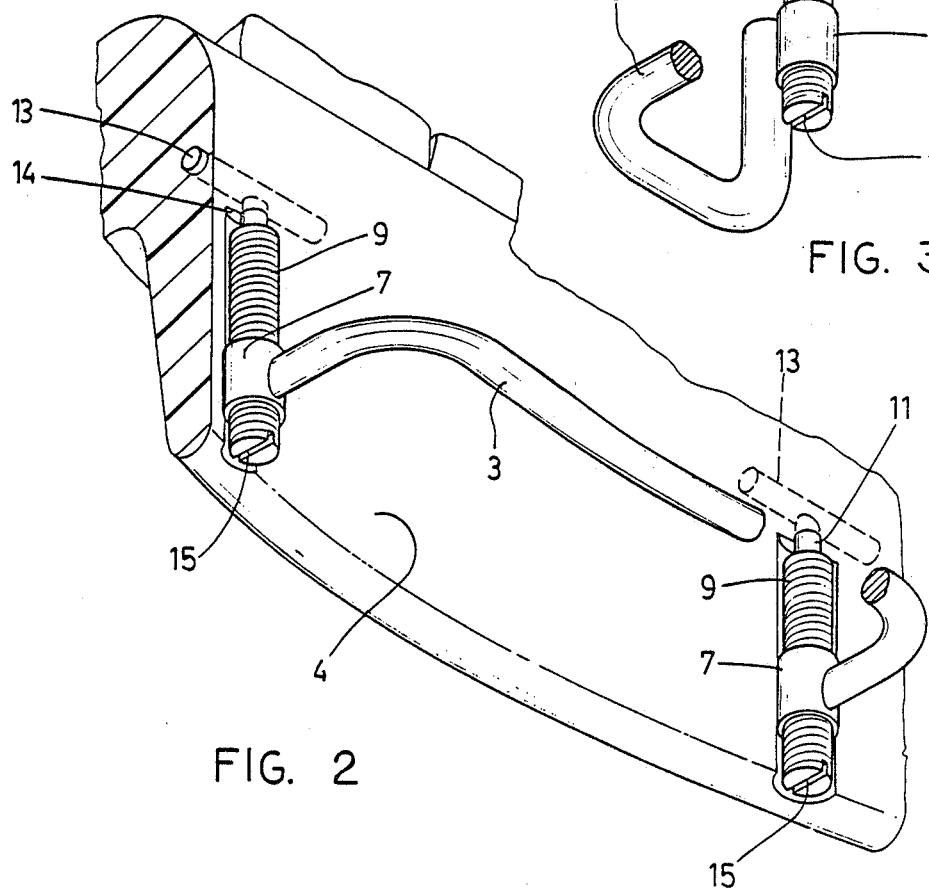
FIG. 2 illustrates the screw type adjusting mechanism for the appendages of this invention.

A screw type adjustable fitting means is illustrated in FIG. 2. Each end of the appendage (3) terminates at a threaded sleeve (7) adapted to receive a threaded shaft (9) (or retention rod) in rotatable connection. The threaded retention rod (9) is mounted rotatably on pintle (11) which is connected to anchor (13) and is adapted to lie within a groove (14) which is ground into the lingual flange (4). Each anchor (13) is adapted to be bonded into the material comprising the lingual flange (4) of the mandibular denture (1). Each shaft is fitted with a slot (15) adapted to receive a screwdriver for adjustment of the appendage (3) by rotation of the shafts (9).

Accordingly, in operation a mandibular denture may be fitted with the appendages (3) by embedding the anchor (13) in the lingual flange (4) in a position determined by measurements of the patient's mouth which will approximately place the appendages (3) in a comfortable position under the patient's tongue. The sleeves (7) may then be fitted onto shaft (9) and the appendages (3) screwed into place by using a screwdriver in slot (15) to turn the shafts (9) to move sleeves (7) along the longitudinal axis of the shafts (9). The denture may then be replaced in the patient's mouth and, by trial and error, adjusted to a position which the patient finds comfortable. The patient may then wear the mandibular denture for a number of days to assure himself that the appendages (3) are properly placed or to make such further adjustments as are necessary. After the patient is satisfied with the fit, materials similar to that of the lingual flange may be used to cover the shaft (9) and sleeve (7) to fix the setting and to protect the shaft (9) and sleeve (7) from food and to prevent irritation of the tongue from rubbing on the rough surface of shaft (9).

Figure 3:
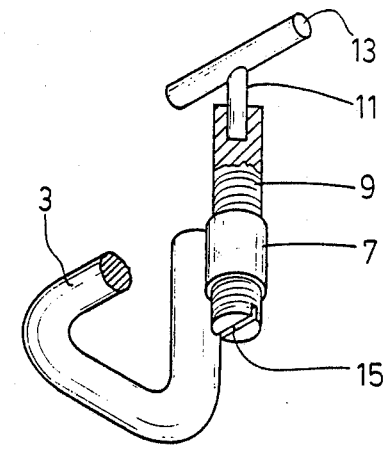
FIG. 3 is a detail of the adjusting mechanism for an embodiment where the appendage depends below the lingual flange.

In FIG. 3, appendage (3) depends from the sleeve (7) before extending laterally inward. This embodiment is useful where the lingual flange (4) does not extend downward sufficiently to use the configuration shown in FIG. 2.

Figure 4:
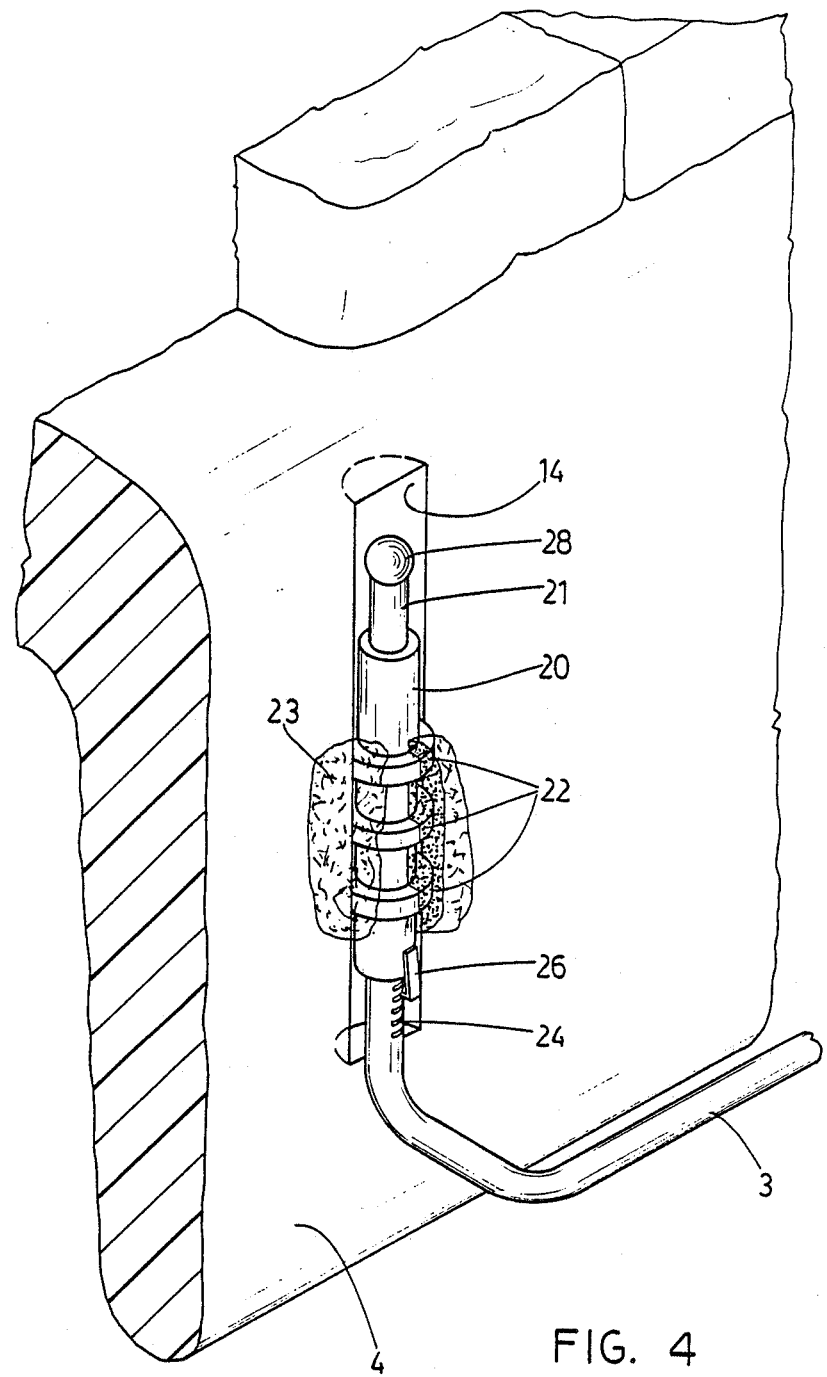
FIG. 4 depicts a friction fit sleeve embodiment of this invention having a fastening means to permit temporary fixation during adjustment.

In another embodiment, shown in FIG. 4, the adjustable fitting means comprises a retention sleeve (20) which is adapted to slide over the ends of the appendages (which become the retention rods (21) in this embodiment) and to be located thereon by friction fit. The exterior sleeve wall is provided with ridges (22) to permit the retention sleeve (20) to be anchored into the lingual flange (4). Bonding material (23) is used to secure the sleeve (20) to the lingual flange (4). Notches

(24) may be provided on retention rods of the appendages (3) to facilitate temporary fixation of the retention rod (21) relates to a retention sleeve (20). The retention sleeve (20) may be provided with a springed edge fastener (26) or like means which is adapted to catch in the notches (24) to effect fixation. A stop (28) is provided at the end of appendage (3) to prevent it from dislodging from the sleeve during fitting. After a comfortable fit is obtained, the whole sleeve, stop and notched portion of the retention rods may be covered with bonding material.

Figure 5:
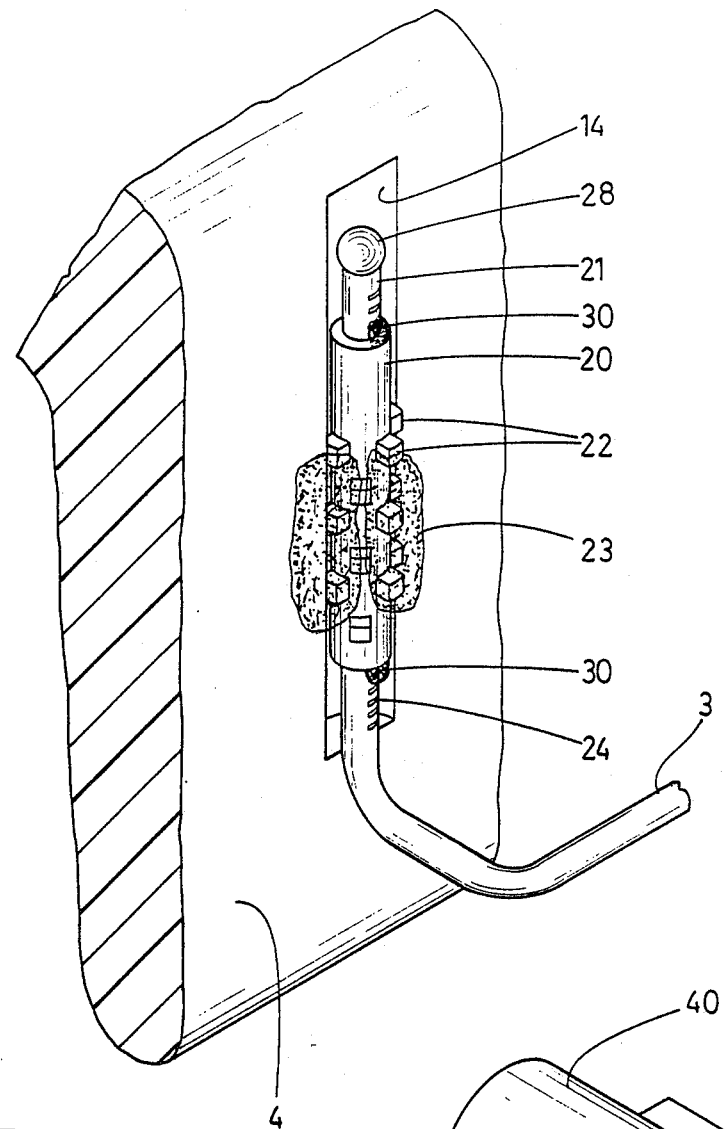
FIG. 5 depicts a sleeve wherein the temporary fixation is achieved by spot bonding with glue or other suitable material.

In FIG. 5, the springed edge fastener (26) is dispensed with and temporary fixation during fitting is achieved by applying a drop of glue or suitable bonding material (30) to the notched shaft of the retention rods (21) at each end of the sleeve (20).

Figure 6:
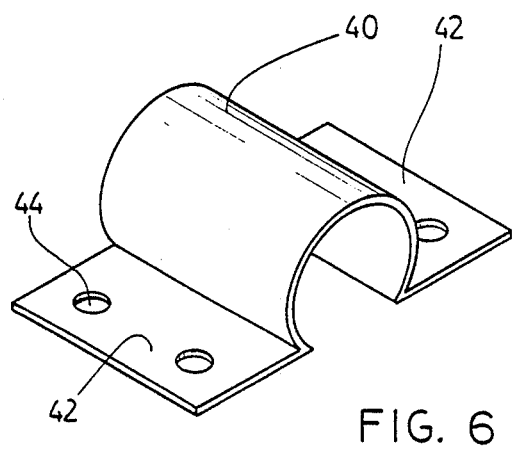
FIG. 6 illustrates an open sided sleeve adapted to be snap fitted over a retention rod of this invention.

In FIG. 6, a sleeve (40) is shown for use in this invention. The sleeve (40) is preferably open along part of its circumference to permit it to be snap fitted over the retention rods (21) of the appendages (3). Each side of the sleeve (40) has flanges (42) having ports (44) adapted to act as anchors. The flanges (42) are bonded into the lingual flange (4) by bonding material (46) as shown in FIG. 7. The ports (44) permit the bonding material (46) to bond through the flanges (42). A retention rod (21) is friction fitted within each sleeve (40) in slidable connection for adjustment. Temporary fixation may be achieved in the manner described above or by other known means.

FIG. 8 shows an alternative to the ball stop (28) shown in the previous Figures. The retention rod (21) may be flattened to provide a lug (50) to prevent slippage through the collar or sleeve means.

In FIG. 9, there is illustrated a appendage (3) having an elliptical cross-section. This is a preferred cross-section in the portion of the appendage which extends under the tongue so as to present a flatter, less irritating surface to the tongue.

Figures 10, 11:
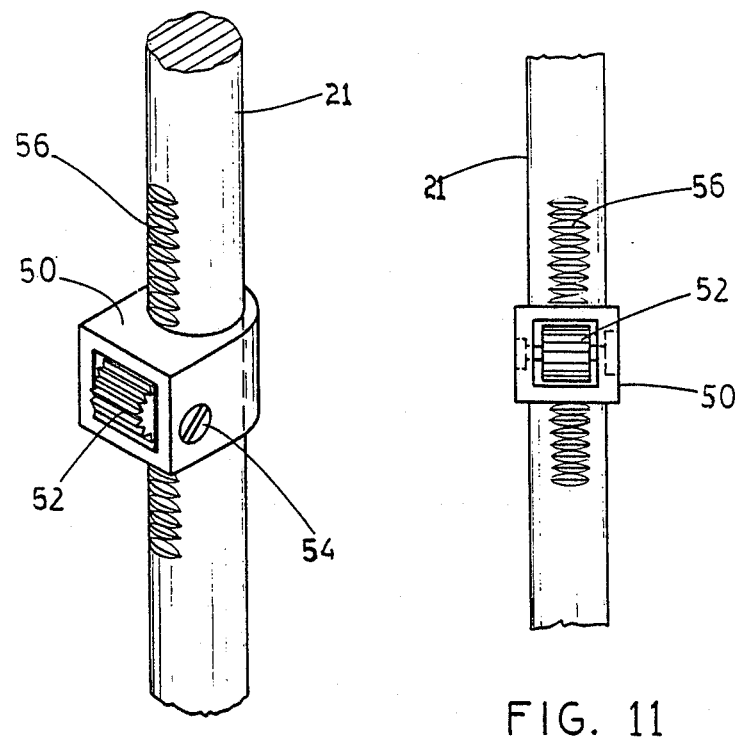
FIG. 10 shows a perspective of a screwdriver gear embodiment.
FIG. 11 shows a side view of the said gear embodiment.

FIGS. 10 and 11 illustrate an embodiment where the end of the appendage having the retention rod (21) is fitted within a retention sleeve (50) containing a gear (52) which may be turned by means of a slotted pin (54). The retention rod (21) is cut with teeth (56) adapted to gear (52) to permit the retention rod (21) to be advanced or retracted by rotating the gear (52) with slotted pin (54).

The retention sleeve (50) may then be embedded in the lingual flange while allowing openings for the retention rod at the top and bottom of the sleeve and over the slotted pin. Then the appendage retention rods may be inserted into the sleeves and advanced to the desired location by rotating the gear with a screw driver inserted into the slotted pin. When the desired fit is obtained, the exposed areas may be covered.

It will be appreciated by those skilled in the art that the open side in FIGS. 10 and 11 is for the purpose of illustrating the gear only. In actual practice, there would be no open side and the gear would be completely enclosed in the sleeve so as not be interfered with by the bonding material.

In the preferred embodiment of this invention, the anterior or front portion of the appendages (3) projects farther inwardly (medially) than the posterior or back portions to lessen irritation to the posterior ventral area of the patient's tongue and the floor of the mouth.

The method of implanting a appendage means of the friction fit type in a denture comprises the steps of:

(a) placing a appendage in a position parallel to an occlusal plane of the denture with a first retention rod located at approximately the mesial of a first bicuspid and a second retention rod of the appendage at approximately the distal of a sixth year molar;

(b) grinding two slots at the location of the retention rods perpendicular to the occlusal plane inferior superiorly into the lingual flange adapted to receive the sleeve and anchor means;

(c) inserting the appendage retention rods into the retention sleeves;

(d) placing retention sleeves into the slots;

(e) applying suitable bonding material to anchor the retention sleeves in place;

(f) adjusting the appendage to the proper location.

After the appendage has been finally set in place, the retention sleeves and retention rods may be covered with suitable bonding material.

It will be appreciated by those skilled in the art that modifications may be made to the embodiments described and illustrated without departing from the scope of this invention.

The embodiments of this invention in which an exclusive property or privilege is claimed are defined as follows:

1. An improved stabilizer for a mandibular denture having an inner depending lingual flange; said stabilizer comprising an anchor means adapted to be secured to said lingual flange, appendage means adapted to fit under the patient's tongue, and fitting means for positively adjusting the position of the appendage means relative to the anchor means.

2. The stabilizer of claim 1 in which the fitting means comprises a threaded sleeve mounted on said appendage means, and a threaded retention rod being rotatably mounted on said anchor means, said retention rod being adapted to be turned in threaded connection within said sleeve to permit adjustment of the position of said appendage means relative to said sleeve.

3. The stabilizer of claim 1 in which the fitting means comprises a threaded sleeve mounted rotatably on said anchor means and a threaded retention rod being mounted on said appendage means, said sleeve being adapted to be turned in threaded connection about said retention rod to permit adjustment of said appendage means relative to said sleeve.

4. The stabilizer of claim 1 in which the fitting means comprises a retention rod having a gear surface which fits within a sleeve means adapted to be anchored within the lingual flanges, said sleeve having a gear within it adapted to be turned against the gear surface of the retention rod to effect adjustment.

5. The stabilizer of claim 4 in which the sleeve means has a fastener adapted to fasten a retention rod of the appendage means for temporary fixation.

6. An improved stabilizer for a mandibular denture having an inner depending lingual flange; said stabilizer comprising sleeve means adapted to be anchored into the lingual flange, appendage means having retention rods being adapted to slidably engage within said sleeve means to permit adjustment, said appendage means being adapted to extend from the lingual flange under a patient's tongue.

7. An improved stabilizer of claim 4 in which the sleeve means is open on one side to permit the appendage means to be snap fitted within it.

8. The stabilizer of claim 6 in which the sleeve means has a fastener adapted to fasten a retention rod of the appendage means for temporary fixation.

9. The method of stabilizing a mandibular denture having a depending lingual flange including;
   (a) placing a appendage in a position parallel to an occlusal plane of the denture with a first retention rod located at approximately the mesial of a first bicuspid and a second retention rod of the appendage at approximately the distal of a sixth year molar;
   (b) grinding two slots at the location of the retention rods perpendicular to the occlusal plane inferior superiorly into the lingual flange;
   (c) inserting the appendage retention rods into the retention sleeves;
   (d) placing retention sleeves into the slots;
   (e) applying suitable bonding material to anchor the retention sleeves in place;
   (f) adjusting the appendage to the proper location.

* * * * *